US010332617B2

(12) United States Patent
Kiel et al.

(10) Patent No.: US 10,332,617 B2
(45) Date of Patent: Jun. 25, 2019

(54) SYSTEMS AND METHODS FOR ELECTRONICALLY MINING GENOMIC DATA

(71) Applicant: THE REGENTS OF THE UNIVERSITY OF MICHIGAN, Ann Arbor, MI (US)

(72) Inventors: Mark J. Kiel, Ann Arbor, MI (US); Kojo Elenitoba-Johnson, Ann Arbor, MI (US); Megan Lim, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 703 days.

(21) Appl. No.: 14/938,509

(22) Filed: Nov. 11, 2015

(65) Prior Publication Data

US 2016/0132506 A1     May 12, 2016

Related U.S. Application Data

(60) Provisional application No. 62/077,956, filed on Nov. 11, 2014.

(51) Int. Cl.
*G16B 20/00* (2019.01)
*G16B 40/00* (2019.01)

(52) U.S. Cl.
CPC .............. *G16B 40/00* (2019.02); *G16B 20/00* (2019.02)

(58) Field of Classification Search
USPC .................................. 702/20; 707/722, 736
See application file for complete search history.

(56) References Cited

U.S. PATENT DOCUMENTS

| | | | |
|---|---|---|---|
| 2008/0097939 A1 | 4/2008 | Guyon et al. | |
| 2012/0053845 A1 | 3/2012 | Bruestle et al. | |
| 2013/0237435 A1 | 9/2013 | Machida et al. | |
| 2013/0332081 A1 | 12/2013 | Reese et al. | |
| 2016/0092631 A1* | 3/2016 | Yandell | G06F 19/22 |
| | | | 702/19 |

OTHER PUBLICATIONS

Extraction of human kinase mutations from literature, databases and genotyping studies Martin Krallinger, Jose MG Izarzugaza†, Carlos Rodriguez-Penagos and Alfonso Valencia, BMC Bioinformatics 2009, pp. 1-20. (Year: 2009).*

(Continued)

*Primary Examiner* — Cheyne D Ly
(74) *Attorney, Agent, or Firm* — Marshall, Gerstein & Borun LLP; Randall G. Rueth

(57) ABSTRACT

A data analysis method and computer system electronically mines published articles from existing medical literature sources to discover associations that may exist between various diseases and various genes and/or gene mutations or other genetic changes. The method and system then organizes, categorizes and prioritizes the discovered associations in accordance with the strength of evidence supporting these associations. The resulting information can then be integrated into the processing of genome sequencing data to more quickly determine what genome sequencing data is of most relevance for clinical decision makings.

14 Claims, 5 Drawing Sheets

(56) References Cited

OTHER PUBLICATIONS

Mutation mining—A prospector's tale Christopher J. O. Baker • Ren'e Witte, Inf Syst Front (2006) 8: 47-57 (Year: 2006).*

Mutation Finder: a high-performance system for extracting point mutation mentions from text J. Gregory Caporaso,*, William A. Baumgartner, Jr, David A. Randolph, K. Bretonnel Cohen and Lawrence Hunter, Bioinformatics, vol. 23 No. 14 2007, pp. 1862-1865 (Year: 2007).*

International Search Report and Written Opinion for Application No. PCT/US2015/060078 dated Feb. 11, 2016.

Manconi et al., "Literature retrieval and mining in bioinformatics: state of the art and challenges", Advances in Bioinformatics, 2012:573846 (2012).

Yepes et al., "Literature mining of genetic variants for curation: quantifying the importance of supplementary material", Database, 2014:bau003 (2014).

International Preliminary Report on Patentability for PCT/US2015/060078 dated May 16, 2017.

\* cited by examiner

FIG. 2A

| Gene | Disease | Articles | Score | Mutation | Loss | Gain | Structural | Upreg | Downreg | Diagnosis | Prognosis | Treatment | Functional | Goldmine | Case Report |
|---|---|---|---|---|---|---|---|---|---|---|---|---|---|---|---|
| BRCA1 | breast cancer | 1905 | 4.2 | | | | | | | | | | | | |
| ATM | ataxia telangioctasia | 1572 | 4.16 | | | | | | | | | | | | |
| APC | polyposis coli | 1308 | 4.07 | | | | | | | | | | | | |
| APC | adenomatous polyposis coli | 1299 | 4.07 | | | | | | | | | | | | |
| BRCA2 | breast cancer | 1226 | 4.02 | | | | | | | | | | | | |
| EGFR | lung cancer | 1431 | 3.98 | | | | | | | | | | | | |

FIG. 2B

|  | Gene 1 | Gene 2 | Gene 3 | Gene 4 | Gene 5 | Gene 6 | ... | Gene X |
|---|---|---|---|---|---|---|---|---|
| Disease 1 | 0 | 2 | 0 | 0 | 0 | 0 | . | 0 |
| Disease 2 | 0 | 0 | 12 | 0 | 0 | 0 | . | 0 |
| Disease 3 | 0 | 0 | 5 | 0 | 0 | 0 | . | 0 |
| Disease 4 | 0 | 0 | 0 | 25 | 10 | 0 | . | 0 |
| ... | . | . | . | . | . | . |  | . |
| Disease Y | 0 | 0 | 0 | 0 | 0 | 0 | . | 5 |

FIG. 4A

| Gene X | Position 1 | Position 2 | Position 3 | Position 4 | Position 5 | Position 6 | ... | Position Z |
|---|---|---|---|---|---|---|---|---|
| Disease Y | 0 | 0 | 0 | 4 | 1 | 0 | . | 0 |

FIG. 4B

SYSTEMS AND METHODS FOR ELECTRONICALLY MINING GENOMIC DATA

CROSS-REFERENCE TO RELATED APPLICATIONS

This application claims the benefit of U.S. Provisional Patent Application No. 62/077,956, entitled "Systems and Methods for Electronically Mining Genomic Data," filed on Nov. 11, 2014, the disclosure of which is hereby incorporated herein by reference.

TECHNICAL FIELD

The present disclosure relates to data mining and, in particular, to systems and methods for electronically mining genomic data from medical literature sources.

BACKGROUND

Genes are the functional unit of human biology and are encoded in DNA sequence. Collectively, the sequence of all DNA including all genes from any individual is called a genome. Recent technological advances have allowed researchers to determine the sequence of entire genomes rapidly and inexpensively, which is revolutionizing the process of discovery in biomedical research and paving the way for the implementation of personalized medicine in clinical practice.

The sequencing of genomes in individual patients can yield important information regarding disease states, diagnoses, prognostics, and various treatment options. Information contained in genome sequencing data is usually vast and complex. However, many medical professionals (e.g., physicians) are primarily concerned with specific clinical questions and thus would like to have targeted information with regard to identified symptoms or suspected diseases. Accordingly, the ability to quickly determine the most clinically or biologically relevant information in the genome sequencing data will allow medical professionals to more quickly provide patients with individualized diagnosis and treatment of diseases.

Interpreting information in the genome sequencing data generally entails relating the information to established genomic data found in medical literature sources. However, this discovery process can be rather tedious and time-consuming, and often requires the expertise of highly-trained experts. Various attempts have been made to automate this process, but there still lacks a widely accepted technique or tool that can effectively and efficiently harness relevant genomic data from existing medical literature sources.

SUMMARY

The features and advantages described in this summary and the following detailed description are not all-inclusive. Many additional features and advantages will be apparent to one of ordinary skill in the art in view of the drawings, specification, and claims hereof. Additionally, other embodiments may omit one or more (or all) of the features and advantages described in this summary.

A computer-implemented method for electronically mining genomic data may include receiving, by one or more processors, reference genomic data that comprises a plurality of published articles obtained from a plurality of medical literature sources. The method may also include receiving, by one or more processors, disease data that comprises one or more types of diseases and gene data that comprises one or more types of genes. Further, the method may include performing, by one or more processors, data mining on the plurality of published articles in the reference genomic data to determine one or more disease-gene associations between at least a portion of the one or more types of diseases in the disease data and at least a portion of the one or more types of genes in the gene data. The method may then store, using one or more processors, the one or more disease-gene associations. Each of the one or more disease-gene associations may specify an association between a particular disease and a particular gene. Next, the method may determine, by one or more processors, at least a portion of possible mutations of the particular gene specified in each of the one or more disease-gene associations. The method may perform, by one or more processors, data mining on the plurality of published articles in the reference genomic data to determine one or more disease-gene-mutation associations between the particular disease and the at least the portion of possible mutations of the particular gene specified in each of the one or more disease-gene associations. The method may also store, using one or more processors, the one or more disease-gene-mutation associations. Finally, the method may prioritize, by one or more processors, the one or more disease-gene associations and the one or more disease-gene-mutation associations based on the strength of evidence provided in the reference genomic data.

A non-transitory computer-readable storage medium may comprise computer-readable instructions to be executed on one or more processors of a system for electronically mining genomic data. The instructions when executed, may cause the one or more processors to receive reference genomic data that comprises a plurality of published articles obtained from a plurality of medical literature sources. The instructions when executed, may also cause the one or more processors to receive disease data that comprises one or more types of diseases and gene data that comprises one or more types of genes. Further, the instructions when executed, may cause the one or more processors to perform data mining on the plurality of published articles in the reference genomic data to determine one or more disease-gene associations between at least a portion of the one or more types of diseases in the disease data and at least a portion of the one or more types of genes in the gene data. The instructions when executed, may then cause the one or more processors to store the one or more disease-gene associations. Each of the one or more disease-gene associations may specify an association between a particular disease and a particular gene. Next, the instructions when executed, may cause the one or more processors to determine at least a portion of possible mutations of the particular gene specified in each of the one or more disease-gene associations. The instructions when executed, may cause the one or more processors to perform data mining on the plurality of published articles in the reference genomic data to determine one or more disease-gene-mutation associations between the particular disease and the at least the portion of possible mutations of the particular gene specified in each of the one or more disease-gene associations. The instructions when executed, may also cause the one or more processors to store the one or more disease-gene-mutation associations. Finally, the instructions when executed, may cause the one or more processors to prioritize the one or more disease-gene associations and the one or more diseasegene-mutation associations based on the strength of evidence provided in the reference genomic data.

A computer system for electronically mining genomic data, the system may comprise a data repository and an analysis server that includes a memory having instructions for execution on one or more processors. The instructions when executed by the one or more processors may cause the analysis server to retrieve reference genomic data from the data repository that comprises a plurality of published articles obtained from a plurality of medical literature sources. The instructions when executed by the one or more processors, may also cause the analysis server to retrieve disease data from the data repository that comprises one or more types of diseases, and retrieve gene data from the data repository that comprises one or more types of genes. Further, the instructions when executed by the one or more processors, may cause the analysis server to perform data mining on the plurality of published articles in the reference genomic data to determine one or more disease-gene associations between at least a portion of the one or more types of diseases in the disease data and at least a portion of the one or more types of genes in the gene data. The instructions when executed by the one or more processors, may then cause the analysis server to store the one or more disease-gene associations in the data repository. Each of the one or more disease-gene associations may specify an association between a particular disease and a particular gene. Next, the instructions when executed by the one or more processors, may cause the analysis server to determine at least a portion of possible mutations of the particular gene specified in each of the one or more disease-gene associations. The instructions when executed by the one or more processors, may cause the analysis server to perform data mining on the plurality of published articles in the reference genomic data to determine one or more disease-gene-mutation associations between the particular disease and the at least the portion of possible mutations of the particular gene specified in each of the one or more disease-gene associations. The instructions when executed by the one or more processors, may also cause the analysis server to store the one or more disease-gene-mutation associations in the data repository. Finally, the instructions when executed by the one or more processors, may cause the analysis server to prioritize the one or more disease-gene associations and the one or more disease-gene-mutation associations based on the strength of evidence provided in the reference genomic data.

BRIEF DESCRIPTION OF THE DRAWINGS

FIGS. 2A and 2B are example screenshots that illustrate a version of the results of electronically mining genomic data from medical literature sources.

FIGS. 4A and 4B are diagrams that illustrate an example process of determining associations between various diseases and various genes and gene mutations.

The figures depict a preferred embodiment of the present invention for purposes of illustration only. One skilled in the art will readily recognize from the following discussion that alternative embodiments of the structures and methods illustrated herein may be employed without departing from the principles of the invention described herein.

DETAILED DESCRIPTION

The systems and methods disclosed herein generally relate to using data mining techniques to electronically mine genomic data from existing medical literature sources. In particular, published articles are harvested and analyzed for associations between various diseases and various genes or gene mutations or other genetic changes including but not limited to changes in copy-number or structural alterations such as translocations. Discovered associations are then organized and prioritized according to the strength of evidence provided by the articles. The whole process is performed autonomously and thus represents a truly automated knowledge creation of genomic data from existing medical literature sources. The results are useful for interpreting genome sequencing data in various settings such as clinical settings for identifying diseases for which a patient is most at risk, in academic settings for use in collecting and understanding varying evidences for genetic associations from a huge variety of primary literature sources, and/or in commercial research settings for facilitating discoveries by identifying the best-supported genetic associations. Furthermore, the results may undergo a process of manual review by one or more reviewers. For example, a reviewer may examine and evaluate the results in a wiki-style interactive environment. This helps to further qualify or improve the automated knowledge creation process.

Figure 1:
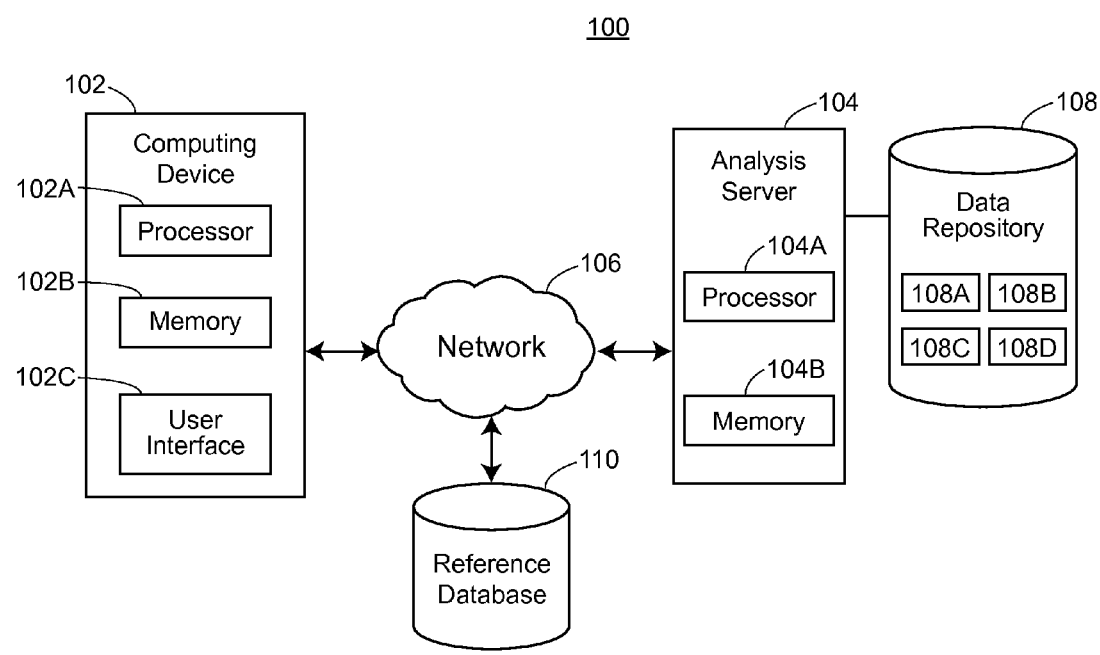
FIG. 1 is a block diagram of an example system for electronically mining genomic data from medical literature sources.

Referring first to FIG. 1, which shows a block diagram of an example system 100 for electronically mining genomic data from medical literature sources. The example system 100 includes a computing device 102 having a processor 102A, a memory 102B and a user interface 102C that is coupled to an analysis server 104 via a communication network 106. The communication network 106 may include any number of wired and/or wireless links. The computing device 102 may be, for example, a laptop computer, a desktop computer, a tablet computer, etc. The analysis server 104 may be a single server or a plurality of servers with distributed processing. The server 104 may be directly coupled to a data repository 108. In some embodiments, the data repository 108 may not be directly coupled to the server 104, but instead may be accessible by the server 104 via a network such as the network 106.

The analysis server 104 may be configured to electronically mine genomic data from medical literature sources. To accomplish this, a processor 104A of the server 104 may execute instructions stored in a memory 104B of the server 104 to first harvest various published articles (e.g., journal papers, reviews, symposia, dissertations, etc.). The articles may be obtained from a reference database 110, which may include any publicly accessible database that stores or archives published medical literatures (e.g., PubMed). The articles may be in any suitable format such as text, PDF, HTML, JPEG, etc. Once obtained, the articles may be stored in the repository 108 as reference genomic data 108A. In some embodiments, the analysis server 104 may be configured to gather articles from the reference database 110 at regular intervals (e.g., at various times throughout each week, each month, etc.). In other embodiments, articles may be automatically requested and sent from the reference database 110 to the server 104 through the use of a refresh executable or script. In this manner, the reference genomic data 108A can be continuously refreshed as the database 110 is updated with newly published or disclosed articles.

The analysis server 104 may then perform data mining on the reference genomic data 108A. More particularly, the server 104 may analyze various genomic information and data described in the articles of the data 108A in order to discover or determine meaningful associations, correlations or links between various types of diseases and various types of genes or gene mutations. In an embodiment, the server 104 may perform data mining by using a text-based querying process based on regular expressions and natural language processing. For example, the server 104 may search text in the title, abstract and/or body of the articles as well as other information (e.g., metadata, text data, etc.) extracted from the articles (e.g., from images, tables or figures in the articles) in order to determine associations between specified diseases and genes or gene mutations.

The various types of diseases may be obtained from a list of known diseases, which is stored in the repository 108 as disease data 108B. Similarly, the various types of genes or gene mutations may be obtained from a list of known genes and mutations, which is stored in the repository 108 as gene data 108C. Accordingly, the server 104 may perform data mining on the reference genomic data 108A to determine any or all associations (e.g., disease-gene and/or disease-gene-mutation associations) that may exist between each type of disease specified in the disease data 108B and each type of gene or gene mutation specified in the gene data 108C. In some embodiments, the server 104 may perform data mining to determine any or all associations that may exist between at least a portion of the various types of diseases specified in the disease data 108B and at least a portion of the various types of genes specified in the gene data 108C.

Generally, the data 108B and 108C may be automatically compiled by using information from external databases (not shown) that archive known diseases, genes and gene mutations. However, if a new disease or gene or gene mutation is discovered during the data mining process, then this information may be automatically added to or saved as part of the data 108B and 108C.

Discovered disease-gene and/or disease-gene-mutation associations are stored in the repository 108 as genomic association data 108D. For example, based on mining the reference genomic data 108A, the analysis server 104 may determine a disease-gene association between breast cancer and the gene BRCA1, or a disease-gene-mutation association between hairy cell leukemia and the V600E mutation of the gene BRAF. Accordingly, these discovered associations may be saved as part of the genomic association data 108D.

Further, each discovered association in the data 108D may be assessed in terms of the strength of evidence provided in the reference genomic data 108A. That is, how much support is found in the data 108A to substantiate the concept that a particular disease is associated with a particular gene or a particular mutation of the gene. For example, if there are thousands of articles in the reference genomic data 108A that describe a particular disease-gene association, then the strength of evidence may be considered strong. On the other hand, if there are only a handful of articles in the reference genomic data 108A that describe the particular disease-gene association, then the strength of evidence may be considered moderate. Other parameters may also be used to define the strength of evidence provided in the reference genomic data 108A. For example, the parameters may relate to evaluating the quality of the articles included in the data 108A in terms of the article types, article impact factors, citations by other articles, publication dates, keywords in the articles, etc. Moreover, based on the strength of evidence, each discovered association in the data 108D may be assigned a priority score which can be used for ranking purposes. In this manner, the server 104 can efficiently organize, categorize and prioritize each discovered genomic association in the data 108D.

The server 104 may display the results of the data mining process to a user. Accordingly, the user may use the computing device 102 to communicate with the server 104 to access and view the results. FIGS. 2A and 2B show example screenshots that illustrate a version of the results of electronically mining genomic data from medical literature sources. In particular, FIG. 2A depicts an overview page 202, which lists various disease-gene associations 204-209 ranked from strongest to weakest. In the embodiment of FIG. 2A, the ranking is based on a number of articles 210 as assessed by counting the number of articles for each of the disease-gene associations 204-209 in which both the disease name and the gene name appear in the title, abstract, and/or full text of the articles. Further, the disease-gene associations 204-209 in FIG. 2A may be ranked according to a priority score 212. In an embodiment, the priority score 212 may be determined by evaluating the quality of all the articles associated with each of the disease-gene associations 204-209.

FIG. 2B illustrates a detailed view of a particular disease-gene association. Specifically, FIG. 2B depicts an evidence page 214 for the disease-gene association 204 shown in FIG. 2A. The evidence page 214 may be generated when the user clicks on the disease-gene association 204 listed in the overview page 202, for example. The evidence page 214 presents an organized view of all the articles and associated metadata related to the disease-gene association 204. For example, the articles may be arranged according to various categories 216-226, such as articles about diagnosis 216, articles about treatment 219, articles appearing in the best journals 221, most recently published articles 223, and the like. Further, for each of the categories 216-226, the total number of articles in each category is given along with a brief description about the content of each article in each of the categories 216-226.

Returning to FIG. 1, in some embodiments, the computing device 102 may be configured to electronically mine genomic data from medical literature sources. In this scenario, the processor 102A may execute instructions stored in the memory 102B to first retrieve the data 108A-108C from the repository 108, and then perform data mining on the data 108A to determine any or all associations that may exist between the various diseases and genes specified in the data 108B and 108C, respectively. Discovered associations may be organized and saved as the data 108D in the repository 108. The discovered associations may be displayed to the user for viewing (e.g., via the user interface 102C of the computing device 102).

Figure 3:
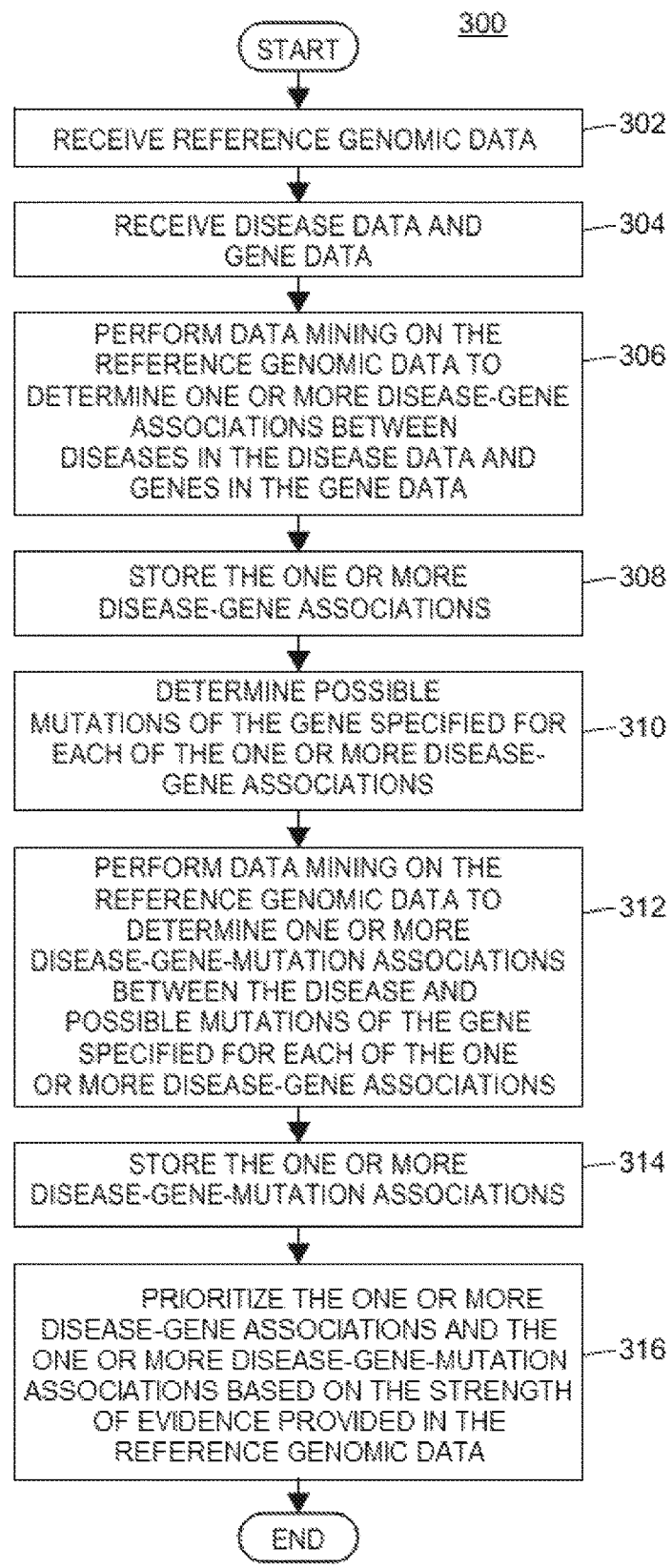
FIG. 3 is a flow diagram of an example method for electronically mining genomic data from medical literature sources.

Referring now to FIG. 3, which describes a flow diagram of an example method 300 for electronically mining genomic data from medical literature sources. The method 300 may include one or more blocks, routines or functions in the form of computer executable instructions that are stored in a tangible computer-readable medium (e.g., 104B, 102B of FIG. 1) and executed using a processor (e.g., 104A, 102A of FIG. 1).

The method 300 begins by receiving reference genomic data (block 302). For example, with reference to FIG. 1, the method 300 may receive the reference genomic data 108A. The reference genomic data may comprise a plurality of published articles gathered from medical literature sources such as publicly accessible databases that store or archive articles pertaining to medicine, biology, and/or other related sciences. The reference genomic data may present, describe, or otherwise provide various genomic information and data as obtained from experiments, clinical trials, statistical analyses, case studies, etc. In general, the method 300 may convert the reference genomic data into any desired format, protocol, or information type needed for subsequent processing.

The method 300 also receives disease data and gene data (block 304). For example, with reference to FIG. 1, the method 300 may receive the disease data 108B and the gene data 108C. The disease data may include a list of one or more known diseases or diseases of interest (e.g., breast cancer, hairy cell leukemia, colorectal carcinoma, lung cancer, etc.) including specific histopathological diagnostic entities (e.g., rhabdoalveolar myosarcoma, glioblastoma multiforme, primary cutaneous diffuse large B-cell lymphoma leg-type, etc.), while the gene data may include a list of one or more known genes or genes of interest (e.g., BRCA1, ATM, FAS, APC, etc.) or other DNA elements. The disease data and the gene data may be automatically compiled from external databases that store or archive known diseases, genes and gene mutations. While the embodiment of FIG. 3 shows the blocks 302 and 304 as being in series, in other embodiments, these blocks may be executed in parallel. For example, the method 300 may receive the reference genomic data, disease data, and gene data simultaneously.

Next, the method 300 proceeds to perform data mining on the reference genomic data to determine one or more disease-gene associations that may exist between diseases specified in the disease data and genes specified in the gene data (block 306). To do so, the method 300 may perform text mining to search the title, abstract and/or body of the articles. Further, the method 300 may extract other information from images, tables or figures included in the articles. From these, the method 300 may determine one or more disease-gene associations between each type of disease specified in the disease data and each type of gene specified in the gene data. In some embodiments, the method 300 may determine one or more disease-gene associations between at least a portion of the diseases specified in the disease data and at least a portion of the genes specified in the gene data. In any event, the method 300 may search and analyze all the published articles (or at least a portion of all the published articles) in the reference genomic data to determine the one or more disease-gene associations. To illustrate this concept, consider FIG. 4A, which depicts the process of determining associations between various diseases and genes in view of the reference genomic data. In FIG. 4A, one or more diseases 402 (e.g., Disease 1 to Disease Y) appear on the leftmost column while one or more genes 404 (e.g., Gene 1 to Gene X) appear on the topmost row. The one or more diseases 402 and genes 404 may be obtained from the disease and gene data received in block 304. Each box in FIG. 4A represents a search or query of the reference genomic data using both a disease term and a gene term. For example, "Disease 1" may represent the disease term "hairy cell leukemia" and "Gene 2" may represent the gene term "BRAF." Thus, the box connecting "Disease 1" and "Gene 2" (e.g., box 406) represents the result of a search of all the articles in reference genomic data for the disease and gene terms. In the embodiment of FIG. 4A, the number inside the box 406 indicates the total number of articles in the reference genomic data that have both the disease term ("hairy cell leukemia") and the gene term ("BRAF") in the title, abstract and/or full text of the articles.

In this manner, each box in FIG. 4A shows the result of data mining the reference genomic data by using each of the one or more diseases 402 and each of the one or more genes 404. As shown in FIG. 4A, "Disease 1" is only associated with "Gene 2." Each of "Disease 2" and "Disease 3" is only associated with "Gene 3." Further, "Disease 4" is associated with "Gene 4" and "Gene 5," while "Disease Y" is only associated with "Gene X." As FIG. 4A illustrates, a particular disease may be associated with multiple different genes (or a particular gene may be associated with multiple different diseases). For example, breast cancer may be associated with the genes BRCA1, BRCA2, and/or EGFR. Likewise, the gene EGRF may be associated with lung and breast cancers.

Returning to FIG. 3, the method 300 then stores the one or more disease-gene associations (block 308). For example, with reference to FIG. 4A, the method 300 may store all boxes in FIG. 4A that have non-zero entries as these boxes represent all meaningful disease-gene associations that have been discovered so far. The method 300 may store all the discovered associations as part of the data 108D in FIG. 1, for example.

The method 300 may determine possible mutations of the gene specified in each of the one or more disease-gene associations (block 310). A gene mutation is a permanent change in the DNA sequence that makes up a gene. Mutations can range in size from a single DNA building block to a large segment of a chromosome. In any event, the risk of developing a disease can greatly increase if mutations occur in a gene associated with the disease. In some embodiments, the method 300 may determine every possible mutation of the gene specified in each of the one or more disease-gene associations. In other embodiments, the method 300 may determine at least a portion of every possible mutation of the gene specified in each of the one or more disease-gene associations.

Further, in the field of genetics, a mutation has a specific operational definition, which does not include other genetic changes, such as translocations or polymorphisms, either of which can also contribute to disease. As such, the possible mutations determined by the method 300 refer to mutations as defined in genetics, which may be any genetic lesion sequence different from a reference standard. However, in other embodiments, the possible mutations determined by the method 300 may include the other genetic changes as described above.

Subsequently, the method 300 may perform data mining on the reference genomic data to determine one or more disease-gene-mutation associations that may exist between the disease and the possible mutations of the gene specified for each of the one or more disease-gene associations (block 312). This represents a further analysis of all the published articles (or at least a portion of all the published articles) in the reference genomic data. To illustrate this concept, consider FIG. 4B, which depicts the process of determining associations between a disease and gene mutations in view of the reference genomic data. In particular, FIG. 4B is shown with reference to FIG. 4A, where a particular disease-gene association (i.e., association between Disease Y and Gene X) is further analyzed to determine associations between the disease and mutations in the gene. In FIG. 4B, various positions 408 (e.g., Position 1 to Position Z) of the "Gene X" appear on the topmost row. As such, each position represents a possible mutation of the "Gene X." Information for the various positions 408 may be obtained from the gene data received in block 304, for example.

Each box in FIG. 4B represents a search or query of the reference genomic data using the disease term and a gene mutation term. Accordingly, the number inside each box indicates the total number of articles in the reference genomic data that have both the disease term and the gene mutation term (e.g., in the title and/or abstract of the articles). As shown in FIG. 4B, "Disease Y" is associated with "Position 4" and "Position 5" of the "Gene X." Taken together, FIGS. 4A and 4B depict a three-dimensional matrix that lists the search results for all the articles in the reference genomic data by using the disease terms, gene terms and gene mutation terms.

Returning again to FIG. 3, the method 300 also stores the one or more disease-gene-mutation associations (block 314). For example, with reference to FIG. 4B, the method 300 may store all boxes in FIG. 4B that have non-zero entries as these boxes represent all meaningful disease-gene-mutation associations that have been discovered so far. The method 300 may store all the discovered associations as part of the data 108D in FIG. 1, for example.

The method 300 then prioritizes the one or more disease-gene associations and the one or more disease-gene-mutation associations based on the strength of evidence provided in the reference genomic data (block 316). Specifically, the method 300 determines how much support is given or found in the articles of the reference genomic data to substantiate the discovered disease-gene and disease-gene-mutation associations. For example, the method 300 may assess the quality of the articles for each of the disease-gene and disease-gene mutation associations as measured by one or more article parameters or any combination of the one or more article parameters such as but not limited to the type of articles, dates of publication, the quality of data presented in the articles, the quality of journal the articles are published in, citations by other articles, impact factor of the articles, keywords in the articles, additional keywords, etc. Moreover, each of the disease-gene and/or disease-gene-mutation associations may be ranked in terms of how strong the association is based on the determined strength of the evidence.

Finally, the method 300 may include additional blocks not shown in FIG. 3. For example, upon a user request or inquiry, the method 300 may generate visualizations for the ranked disease-gene and disease-gene-mutation associations, and then display the visualizations to the user (e.g., via the computing device 102 of FIG. 1).

Figure 5:
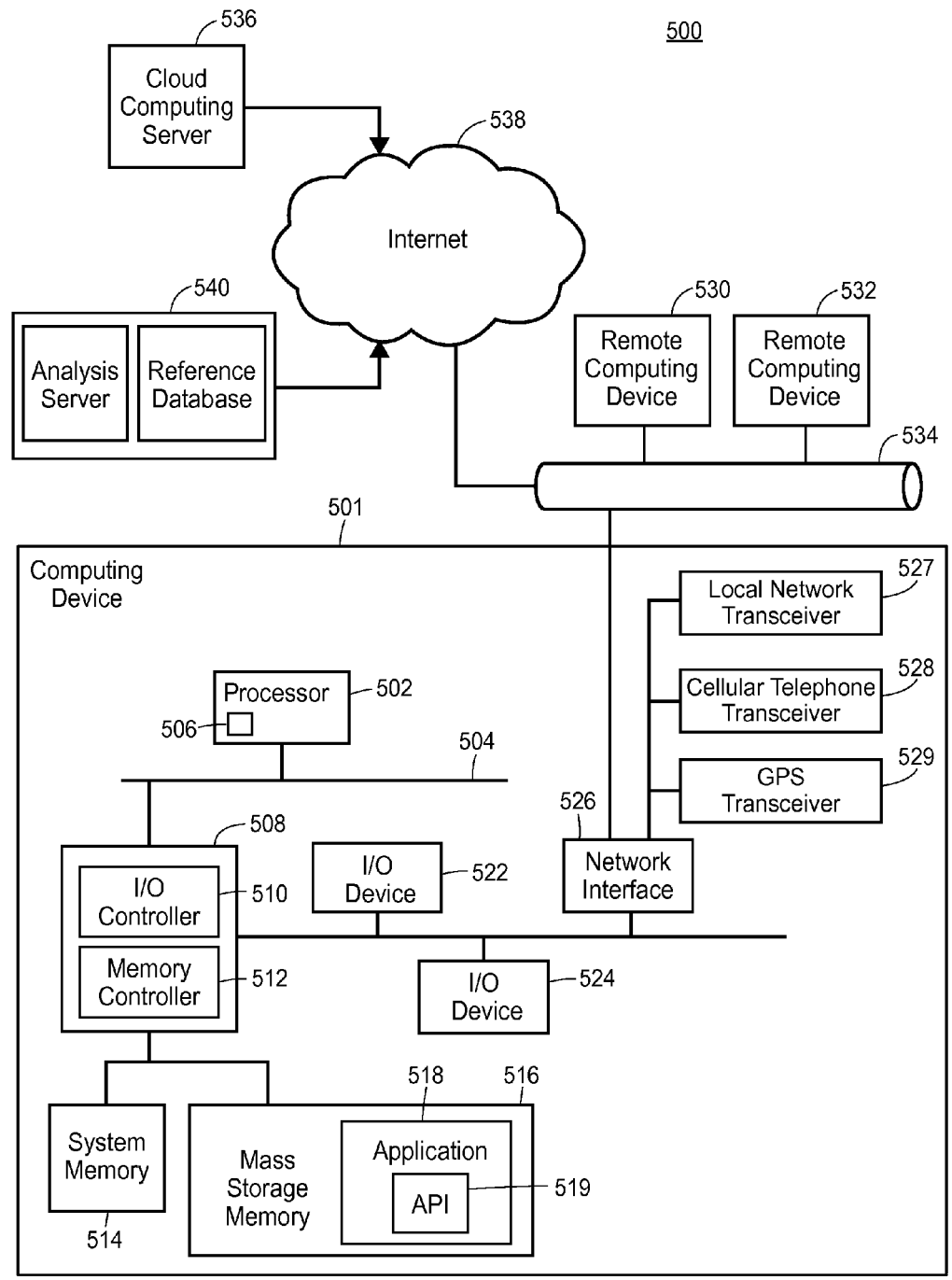
FIG. 5 is a block diagram of a computing environment that implements a system and method for electronically mining genomic data from medical literature sources.

FIG. 5 is a block diagram of an example computing environment for an analysis system 500 having a computing device 501 that may be used to implement the systems and methods described herein. The computing device 501 may include one or more computing devices 102 (e.g., a desktop computer, a laptop computer, a tablet computer, etc.), a server 104 or other personal computing device capable of wireless or wired communication. As will be recognized by one skilled in the art, in light of the disclosure and teachings herein, other types of computing devices can be used that have different architectures. Processor systems similar or identical to the example analysis system 500 may be used to implement and execute the example system of FIG. 1, the method of FIG. 3, and the like. Although the example analysis system 500 is described below as including a plurality of peripherals, interfaces, chips, memories, etc., one or more of those elements may be omitted from other example processor systems used to implement and execute the example system 100. Also, other components may be added.

As shown in FIG. 5, the computing device 501 includes a processor 502 that is coupled to an interconnection bus 504. The processor 502 includes a register set or register space 506, which is depicted in FIG. 5 as being entirely on-chip, but which could alternatively be located entirely or partially off-chip and directly coupled to the processor 502 via dedicated electrical connections and/or via the interconnection bus 504. The processor 502 may be any suitable processor, processing unit or microprocessor. Although not shown in FIG. 5, the computing device 501 may be a multi-processor device and, thus, may include one or more additional processors that are identical or similar to the processor 502 and that are communicatively coupled to the interconnection bus 504.

The processor 502 of FIG. 5 is coupled to a chipset 508, which includes a memory controller 510 and a peripheral input/output (I/O) controller 512. As is well known, a chipset typically provides I/O and memory management functions as well as a plurality of general purpose and/or special purpose registers, timers, etc., that are accessible or used by one or more processors coupled to the chipset 508. The memory controller 510 performs functions that enable the processor 502 (or processors if there are multiple processors) to access a system memory 514 and a mass storage memory 516, that may include either or both of an in-memory cache (e.g., a cache within the memory 514) or an on-disk cache (e.g., a cache within the mass storage memory 516).

The system memory 514 may include any desired type of volatile and/or non-volatile memory such as, for example, static random access memory (SRAM), dynamic random access memory (DRAM), flash memory, read-only memory (ROM), etc. The mass storage memory 516 may include any desired type of mass storage device. For example, if the computing device 501 is used to implement an application 518 having an API 519 (including functions and instructions as described by the method 300 of FIG. 3). The mass storage memory 516 may include a hard disk drive, an optical drive, a tape storage device, a solid-state memory (e.g., a flash memory, a RAM memory, etc.), a magnetic memory (e.g., a hard drive), or any other memory suitable for mass storage. As used herein, the terms module, block, function, operation, procedure, routine, step, and method refer to tangible computer program logic or tangible computer executable instructions that provide the specified functionality to the computing device 501 and the analysis system 500. Thus, a module, block, function, operation, procedure, routine, step, and method can be implemented in hardware, firmware, and/or software. In one embodiment, program modules and routines (e.g., the application 518, the API 519, etc.) are stored in mass storage memory 516, loaded into system memory 514, and executed by a processor 502 or can be provided from computer program products that are stored in tangible computer-readable storage mediums (e.g., RAM, hard disk, optical/magnetic media, etc.).

The peripheral I/O controller 510 performs functions that enable the processor 502 to communicate with peripheral input/output (I/O) devices 522 and 524, a network interface 526, a local network transceiver 527, a cellular network transceiver 528, and a GPS transceiver 529 via the network interface 526. The I/O devices 522 and 524 may be any desired type of I/O device such as, for example, a keyboard, a display (e.g., a liquid crystal display (LCD), a cathode ray tube (CRT) display, etc.), a navigation device (e.g., a mouse, a trackball, a capacitive touch pad, a joystick, etc.), etc. The cellular telephone transceiver 528 may be resident with the local network transceiver 527. The local network transceiver 527 may include support for a Wi-Fi network, Bluetooth, Infrared, or other wireless data transmission protocols. In other embodiments, one element may simultaneously support each of the various wireless protocols employed by the computing device 501. For example, a software-defined radio may be able to support multiple protocols via downloadable instructions. In operation, the computing device 501 may be able to periodically poll for visible wireless network transmitters (both cellular and local network) on a periodic basis. Such polling may be possible even while normal wireless traffic is being supported on the computing device 501. The network interface 526 may be, for example, an Ethernet device, an asynchronous transfer mode (ATM) device, an 802.11 wireless interface device, a DSL modem, a cable modem, a cellular modem, etc., that enables the system 100 to communicate with another computer system having at least the elements described in relation to the system 100.

While the memory controller 512 and the I/O controller 510 are depicted in FIG. 5 as separate functional blocks within the chipset 508, the functions performed by these blocks may be integrated within a single integrated circuit or may be implemented using two or more separate integrated circuits. The analysis system 500 may also implement the application 518 on remote computing devices 530 and 532. The remote computing devices 530 and 532 may communicate with the computing device 501 over an Ethernet link 534. In some embodiments, the application 518 may be retrieved by the computing device 501 from a cloud computing server 536 via the Internet 538. When using the cloud computing server 536, the retrieved application 518 may be programmatically linked with the computing device 501. The application 518 may be a Java® applet executing within a Java® Virtual Machine (JVM) environment resident in the computing device 501 or the remote computing devices 530, 532. The application 518 may also be "plug-ins" adapted to execute in a web-browser located on the computing devices 501, 530, and 532. In some embodiments, the application 518 may communicate with backend components 540 such as the analysis server 104 and the reference database 110 via the Internet 538.

The system 500 may include but is not limited to any combination of a LAN, a MAN, a WAN, a mobile, a wired or wireless network, a private network, or a virtual private network. Moreover, while only two remote computing devices 530 and 532 are illustrated in FIG. 5 to simplify and clarify the description, it is understood that any number of client computers are supported and can be in communication within the system 500.

Additionally, certain embodiments are described herein as including logic or a number of components, modules, or mechanisms. Modules may constitute either software modules (e.g., code or instructions embodied on a machine-readable medium or in a transmission signal, wherein the code is executed by a processor) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. As used herein, "hardware-implemented module" refers to a hardware module. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs)).

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "some embodiments" or "an embodiment" means that a particular element, feature, structure, or characteristic described in connection with the embodiment is included in at least one embodiment. The appearances of the phrase "in some embodiments" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Further, the figures depict preferred embodiments of a system and method for electronically mining genomic data from medical literature sources for purposes of illustration only. One skilled in the art will readily recognize from the following discussion that alternative embodiments of the structures and methods illustrated herein may be employed without departing from the principles described herein.

Upon reading this disclosure, those of skill in the art will appreciate still additional alternative structural and functional designs for a system and a process for electronically mining genomic data from medical literature sources through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

We claim:

1. A computer-implemented method for electronically mining genomic data, the method comprising:

receiving, by one or more processors, reference genomic data comprising a plurality of published articles obtained from a plurality of medical literature sources;

receiving, by one or more processors, disease data comprising a list of disease terms associated with one or more types of diseases, receiving, by one or more processors, gene data comprising a list of gene terms associated with one or more types of genes;

performing, by one or more processors, data mining on the plurality of published articles in the reference genomic data to determine one or more disease-gene associations between at least a portion of the one or more types of diseases in the disease data and at least a portion of the one or more types of genes in the gene data by identifying each co-occurrence of a disease term of the disease data with a gene term of the gene data occurring in a published article of the reference genomic data;

storing, using one or more processors, the one or more disease-gene associations, wherein each of the one or more disease-gene associations specifies an association between a particular disease and a particular gene;

determining, by one or more processors, at least a portion of possible mutations or other genetic changes of the particular gene specified in each of the one or more disease-gene associations as a compendium of mutation-related entries associated with such possible mutations or other genetic changes;

performing, by one or more processors, data mining on the plurality of published articles in the reference genomic data to determine one or more disease-gene-mutation associations between the particular disease and the at least the portion of possible mutations of the particular gene specified in each of the one or more disease-gene associations by identifying each occurrence of a mutation-related entry of the comprehensive compendium associated with the one or more disease-gene associations occurring in a published article of the reference genomic data;

storing, using one or more processors, the one or more disease-gene-mutation associations;

generating, by one or more processors, a priority score for each of the one or more disease-gene associations and the one or more disease-gene-mutation associations based upon (i) a total number of published articles identified for each of the one or more disease-gene associations or for each of the one or more disease-gene-mutation associations and (ii) one or more of the following article parameters indicative of quality of each published article: a number of keywords in the published article, a number of citations of the published article by other articles, an article type of the published article, or a publication date of the published article; and prioritizing, by one or more processors, the one or more disease-gene associations and the one or more disease-gene-mutation associations according to the strength of evidence provided in the reference genomic data by ranking the one or more disease-gene associations and the one or more disease-gene-mutation associations according to the respective priority score of each of the one or more disease-gene associations and the one or more disease-gene-mutation associations.

2. The computer-implemented method of claim 1, wherein performing data mining to determine the one or more disease-gene associations further includes determining a total number of articles for each of the one or more disease-gene associations, wherein the total number of articles is determined by searching at least a portion of the plurality of published articles in the reference genomic data for articles that include both the particular disease and particular gene in one or more of a title an abstract, or a full text of the articles.

3. The computer-implemented method of claim 1, wherein performing data mining to determine the one or more disease-gene-mutation associations further includes determining a total number of articles for each of the one or more disease-gene-mutation associations, wherein the total number of articles is determined by searching at least a portion of the plurality of published articles in the reference genomic data for articles that include both the particular disease and the at least the portion of possible mutations of the particular gene in one or more of a title, an abstract, or a full text of the articles.

4. The computer-implemented method of claim 1, wherein the one or more article parameters further include an impact factor of the article.

5. The computer-implemented method of claim 1, further comprises displaying the ranked one or more disease-gene associations and the ranked one or more gene-disease-mutation associations to a user.

6. A non-transitory computer-readable storage medium including computer-readable instructions to be executed on one or more processors of a system for electronically mining genomic data, the instructions when executed causing the one or more processors to:

receive reference genomic data comprising a plurality of published articles obtained from a plurality of medical literature sources;

receive disease data comprising a list of disease terms associated with one or more types of diseases;

receive gene data comprising a list of gene terms associated with one or more types of genes;

perform data mining on the plurality of published articles in the reference genomic data to determine one or more disease-gene associations between at least a portion of the one or more types of diseases in the disease data and at least a portion of the one or more types of genes in the gene data by identifying each co-occurrence of a disease term of the disease data with a gene term of the gene data occurring in a published article of the reference genomic data;

store the one or more disease-gene associations, wherein each of the one or more disease-gene associations specifies an association between a particular disease and a particular gene;

determine at least a portion of possible mutations or other genetic changes of the particular gene specified in each of the one or more disease-gene associations as a compendium of mutation-related entries associated with such possible mutations or other genetic changes;

perform data mining on the plurality of published articles in the reference genomic data to determine one or more disease-gene-mutation associations between the particular disease and the at least the portion of possible mutations of the particular gene specified in each of the one or more disease-gene associations by identifying each occurrence of a mutation-related entry of the comprehensive compendium associated with the one or more disease-gene associations occurring in a published article of the reference genomic data;

store the one or more disease-gene-mutation associations;

generate a priority score for each of the one or more disease-gene associations and the one or more disease-gene-mutation associations based upon (i) a total number of published articles identified for each of the one or more disease-gene associations or for each of the one or more disease-gene-mutation associations and (ii) one or more of the following article parameters indicative of quality of each published article: a number of keywords in the published article, a number of citations of the published article by other articles, an article type of the published article, or a publication date of the published article; and assess the one or more disease-gene associations and the one or more disease-gene-mutation associations according to the strength of evidence provided in the reference genomic data by ranking the one or more disease-gene associations and the one or more disease-gene-mutation associations according to the respective priority score of each of the one or more disease-gene associations and the one or more disease-gene-mutation associations.

7. The non-transitory computer-readable storage medium of claim 6, wherein the instructions to perform data mining to determine the one or more disease-gene associations further include determining a total number of articles for each of the one or more disease-gene associations, wherein the total number of articles is determined by searching at least a portion of the plurality of published articles in the reference genomic data for articles that include both the particular disease and particular gene in one or more of a title, an abstract or a full text of the articles.

8. The non-transitory computer-readable storage medium of claim 6, wherein the instructions to perform data mining to determine the one or more disease-gene-mutation associations further include determining a total number of articles for each of the one or more disease-gene-mutation associations, wherein the total number of articles is determined by searching at least a portion of the plurality of published articles in the reference genomic data for articles that include both the particular disease and the at least the portion of possible mutations of the particular gene in one or more of a title, an abstract, or a full text of the articles.

9. The non-transitory computer-readable storage medium of claim 6, wherein the article parameters further include an impact factor of the article.

10. The non-transitory computer-readable storage medium of claim 6, further including instructions that, when executed, cause the one or more processors to display the ranked one or more disease-gene associations and the ranked one or more gene-disease-mutation associations to a user.

11. A computer system for electronically mining genomic data, the system comprising:
   a data repository; and
   an analysis server, including a memory having instructions for execution on one or more processors, wherein the instructions, when executed by the one or more processors, cause the analysis server to:
      retrieve reference genomic data from the data repository, the reference genomic data comprising a plurality of published articles obtained from medical literature sources;
      retrieve disease data from the data repository, the disease data comprising a list of disease terms associated with one or more types of diseases;
      retrieve gene data from the data repository, the gene data comprising a list of gene terms associated with one or more types of genes;
      perform data mining on the plurality of published articles in the reference genomic data to determine one or more disease-gene associations between at least a portion of the one or more types of diseases in the disease data and at least a portion of the one or more types of genes in the gene data by identifying each co-occurrence of a disease term of the disease data with a gene term of the gene data occurring in a published article of the reference genomic data;
      store the one or more disease-gene associations in the data repository, wherein each of the one or more disease-gene associations specifies an association between a particular disease and a particular gene;
      determine at least a portion of possible mutations or other genetic changes of the particular gene specified in each of the one or more disease-gene associations as a compendium of mutation-related entries associated with such possible mutations or other genetic changes;
      perform data mining on the plurality of published articles in the reference genomic data to determine one or more disease-gene-mutation associations between the particular disease and the at least the portion of possible mutations of the particular gene specified in each of the one or more disease-gene associations by identifying each occurrence of a mutation-related entry of the comprehensive compendium associated with the one or more disease-gene associations occurring in a published article of the reference genomic data;
      store the one or more disease-gene-mutation associations in the data repository;
      generate a priority score for each of the one or more disease-gene associations and the one or more disease-gene-mutation associations based upon (i) a total number of published articles identified for each of the one or more disease-gene associations or for each of the one or more disease-gene-mutation associations and (ii) one or more of the following article parameters indicative of quality of each published article: a number of keywords in the published article, a number of citations of the published article by other articles, an article type of the published article, or a publication date of the published article; and
      assess the one or more disease-gene associations and the one or more disease-gene-mutation associations according to the strength of evidence provided in the reference genomic data by ranking the one or more disease-gene associations and the one or more disease-gene-mutation associations according to the respective priority score of each of the one or more disease-gene associations and the one or more disease-gene-mutation associations.

12. The computer system of claim 11, wherein the instructions of the analysis server when executed by the one or more processors to perform data mining to determine the one or more disease-gene associations further include determining a total number of articles for each of the one or more disease-gene associations, wherein the total number of articles is determined by searching at least a portion of the plurality of published articles in the reference genomic data for articles that include both the particular disease and particular gene in one or more of a title, an abstract, or a full text of the articles.

13. The computer system of claim 11, wherein the instructions of the analysis server when executed by the one or more processors to perform data mining to determine the one or more disease-gene-mutation associations further include determining a total number of articles for each of the one or more disease-gene-mutation associations, wherein the total number of articles is determined by searching at least a portion of the plurality of published articles in the reference genomic data for articles that include both the particular disease and the at least the portion of possible mutations of the particular gene in one or more of a title, an abstract, or a full text of the articles.

14. The computer system of claim 11, wherein the article parameters further include an impact factor of the article.

* * * * *